United States Patent [19]
Galland et al.

[11] Patent Number: 5,707,497
[45] Date of Patent: Jan. 13, 1998

[54] PROCESS FOR THE SEPARATION OF HYDROGEN FLUORIDE AND OF DIFLUOROMETHANE

[75] Inventors: Jean-Michel Galland, Vernaison; Dominique Rouzies, Lyons, both of France

[73] Assignee: Elf Atochem S.A., Puteaux, France

[21] Appl. No.: 394,983

[22] Filed: Feb. 27, 1995

[30] Foreign Application Priority Data

Feb. 28, 1994 [FR] France ................................. 94 02231

[51] Int. Cl.⁶ .......................... B01D 3/36; C07C 17/38
[52] U.S. Cl. ........................ 203/75; 203/77; 203/78; 203/80; 423/483; 423/488; 570/178
[58] Field of Search ..................... 203/1, 3, 75, 77, 203/39, 74, 67, 78, 80; 570/177, 178; 423/483, 488; 252/DIG. 9

[56] References Cited

U.S. PATENT DOCUMENTS 5,196,616  3/1993  Lee et al. ........................... 203/39

FOREIGN PATENT DOCUMENTS 0345671  12/1994  Japan.
033691   2/1995   Japan.
WO A 93
21140    10/1993  WIPO.
9512563  5/1995   WIPO.

*Primary Examiner*—Virginia Manoharan
*Attorney, Agent, or Firm*—Bell, Boyd & Lloyd

[57] ABSTRACT

A process for the separation of hydrogen fluoride (HF) and of difluoromethane (F32) by fractional distillation and/or condensation, in at least one stage, including in at least one stage obtaining a stream whose HF and F32 contents correspond.

9 Claims, 2 Drawing Sheets

PROCESS FOR THE SEPARATION OF HYDROGEN FLUORIDE AND OF DIFLUOROMETHANE

FIELD OF THE INVENTION

The invention relates to the separation of hydrogen fluoride (HF) and of difluoromethane (F32), which is a fluorine compound without effect on the ozone layer and which can therefore be employed as a replacement product for chlorofluorocarbons (CFCs).

The process according to the invention is more particularly intended for the separation of unconverted HF present in the mixtures originating from the manufacture of F32 by fluorination of methylene chloride with HF. In such a manufacture it is, in fact, economically necessary, on the one hand, to recover the unconverted HF in anhydrous form in order to recycle it to the fluorination reactor and, on the other hand, to recover F32 as free as possible from HF, to facilitate its subsequent final purification.

BACKGROUND OF THE INVENTION

Most chlorofluoro- or fluorohydrocarbons form azeotropes with HF; separation of HF and of these compounds is therefore difficult. Various techniques have already been described with the objective of performing this separation. There may be mentioned, for example:

U.S. Pat. No. 2,640,086, which relates to the separation of HF and of chlorodifluoromethane and employs chloroform to promote the separation into two phases, an HF-rich phase and an HF-lean phase;

U.S. Pat. No. 3,873,629, relating to a continuous process for the separation of HF and of chlorodifluoromethane and consisting in bringing the gaseous mixture of the two constituents into contact countercurrentwise with sulphuric acid;

U.S. Pat. No. 3,976,447, which proposes a separation of HF from gaseous effluents by absorption-desorption on particles of calcium, barium or strontium chloride;

U.S. Pat. No. 4,209,470, which describes a process for separation of HF from its mixtures with 1-chloro-1,1-difluoroethane, in which, to improve the phase separation, an auxiliary liquid is added, consisting entirely or predominantly of 1,1-dichloro-1-fluoroethane;

U.S. Pat. No. 5,094,773, relating to the separation of HF from its mixtures with 2,2-dichloro-1,1,1-trifluoroethane and/or 2-chloro-1,1,1,2-tetrafluoroethane by phase separation and distillation;

patent application EP 0,467,531, which describes a process for separation of 1,1,1,2-tetrafluoroethane from its mixtures with HF and/or 1-chloro-2,2-difluoroethylene by double distillation with or without phase separation;

patent application JP 5,178,768, which describes the separation of 1,1,1,2-tetrafluoroethane from its mixtures with HF by double distillation.

These various techniques are either uneconomical or inapplicable to the separation of HF and of F32.

Inspection of known data on the variations with pressure in the composition of the azeotropes of HF and of various chlorofluoro- or fluorohydrocarbons (see Table 1 which follows) shows that the HF content of these azeotropes varies relatively little with pressure. It is found, furthermore, that, in the case of F22 and of F134a, the HF content tends to a limiting value (2.4 and 2.8% respectively) at elevated pressures.

TABLE I

| Chlorofluoro- or fluorohydrocarbon | Pressure (bars absolute) | HF content of the azeotrope (weight %) | Reference |
|---|---|---|---|
| Dichlorodifluoromethane (F12) | 2.8 | 4.5 | 1 |
| | 4.8 | 5.1 | 1 |
| | 7.8 | 8.0 | 1 |
| | 11.3 | 7.5 | 2 |
| Chlorodifluoromethane (F22) | 5.8 | 3 | 2 |
| | 11.3 | 2.7 | 2 |
| | 16.9 | 2.8 | 2 |
| | 25.2 | 2.4 | 3 |
| | 34.6 | 2.4 | 3 |
| 1,1,2-Trichloro-1,2,2-trifluoroethane (F113) | 1.6 | 15.8 | 3 |
| | 9.5 | 20 | 3 |
| 1,2-Dichloro-1,1,2,2-tetrafluoroethane (F114) | 2.9 | 9.5 | 3 |
| | 16.9 | 11.7 | 3 |
| 1,1-Dichloro-2,2,2-trifluoroethane (F123) | 1 | 17 | 4 |
| | 25 | 15.1 | 4 |
| | 40 | 14.9 | 4 |
| 1-Chloro-1,2,2,2-tetrafluoroethane (F124) | 1 | 4.2 | 4 |
| | 25 | 5.8 | 4 |
| | 40 | 5.9 | 4 |
| 1,1,2,2-Tetrafluoroethane (F134a) | 0.5 | 6.8 | 5 |
| | 0.5 | 1.2 | 6 |
| | 1 | 5.8 | 5 |
| | 1 | 1.7 | 6 |
| | 2 | 2.6 | 6 |
| | 3 | 4.1 | 5 |
| | 3 | 3.1 | 6 |
| | 4 | 3.6 | 6 |
| | 5 | 3.9 | 6 |
| | 6 | 3.3 | 5 |
| | 10 | 2.8 | 5 |
| | 16 | 2.8 | 5 |

References:
1 - M. A. Zapol'skaya et al., Teor. Osnovy Khim. Tekh., 1975, pp 3–10
2 - Azeotropic Data, 1973, III, Horsley Lee H., American Chemical Society, Advances in Chemistry Series No. 116, page 11
3 - Applicant's internal data
4 - U.S. Pat. No. 5,094,773
5 - patent application Ser. No. EP 0 467 531
6 - patent application Ser. No. JP 5 178 768

BRIEF DESCRIPTION OF THE DRAWINGS

The invention will now be described with reference to the following non-limiting drawings.

Figure 1:
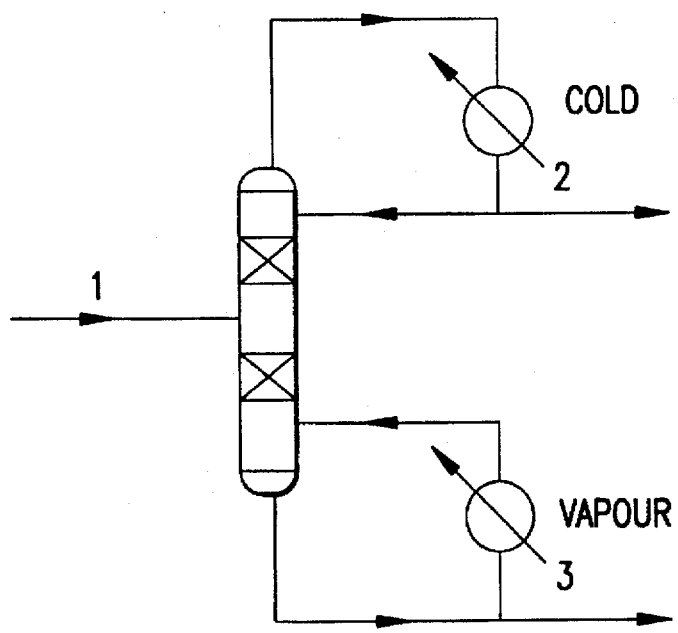
FIGS. 1, 2, 3 and 4 show schematic flow diagrams depicting embodiments of the invention.

It has now been found that, while HF and F32 do form an azeotrope, like most of the chlorofluoro- or fluorohydrocarbons, this HF-F32 azeotrope is singularly characterized (see Table II below) by an HF content which drops considerably when the pressure increases and which becomes very low (lower than 3000 ppm by weight) below 20 bars absolute.

From the data in Table II the pressure Pa of the azeotropic mixture (expressed in bars absolute) can be represented as a function of the HF content x of this mixture (expressed in per cent by weight) by the following relationship:

$$Pa = 17 - 22.9(x+0.821)ln(x+0.608) + 56.6[ln(x+0.608)]^2$$

TABLE II

| PRESSURE (bars absolute) | HF-F32 AZEOTROPE HF CONTENT (weight %) | BOILING TEMPERATURE (°C.) |
| --- | --- | --- |
| 2.7 | 2.6 | −27 |
| 6 | 2.2 | −8.2 |
| 10 | 1 | 7.2 |
| 20 | 0.3 | 33.1 |
| 31 | 0.1 | 51.8 |

This special behaviour of the HF-F32 azeotrope was quite unexpected and can be exploited, in accordance with the present invention, for carrying out industrially effective separations of HF and of F32, especially in order to recover the unconverted HF present in the mixtures originating from the manufacture of F32 by fluorination of methylene chloride with HF, and/or to obtain F32 virtually free from HF.

The subject of the invention is therefore a process for separation of hydrogen fluoride (HF) and of difluoromethane (F32) by fractional distillation and/or condensation, in one or more stages, characterized in that it includes at least one stage making it possible to obtain a stream whose HF and F32 contents correspond substantially to those of the azeotropic composition, the said stage being performed, as a function of the intended separation objective, at a pressure chosen so that the partial pressure of the HF+F32 mixture of the said stream (Pa expressed in bars absolute) and the HF content of the said mixture (x in per cent by weight) are linked by the relationship:

$$Pa = 17 - 22.9(x+0.821)\ln(x+0.608) + 56.6[\ln(x+0.608)]^2$$

The process according to the invention applies not only to the separation of mixtures containing only HF and F32, but also to that of crude mixtures from the manufacture of F32. This manufacture can be performed according to processes that are known per se, which may be:

- either of the so-called liquid-phase type, generally catalyzed homogeneously by antimony chlorofluorides,
- or of the so-called gaseous-phase type, generally catalyzed heterogeneously by a solid catalyst based on various metals, for example chromium.

Besides HF and F32, the mixture to be separated according to the invention may therefore include variable proportions of other products or impurities such as, for example, hydrochloric acid, chlorofluoromethane (F31), chlorodifluoromethane (F22), trifluoromethane (F23), chlorine etc. The mixture to be treated may be available at various pressures, may be gaseous or liquid and may contain variable proportions of HF and of F32.

The process according to the invention may be carried out according to numerous variants, especially those corresponding to the diagrams of the appended FIGS. 1 to 4. The choice of one variant or another by the manufacturer will depend on the nature of the mixture to be treated and on the objective aimed at (recovery of most of the unconverted HF and/or obtaining F32 virtually free from HF).

The method of implementation according to FIG. 1 applies more particularly to the separation of mixtures consisting essentially of HF and of F32 and in which the HF weight content is of the order of several per cent. Such a mixture can be obtained downstream of manufacture of F32 after distillation of hydrochloric acid.

According to this embodiment the mixture to be separated is fed continuously via the conduit (1) into a conventional distillation column and is subjected to a distillation conducted at a pressure above 6 bars absolute, preferably above 10 bars absolute.

A stream (2) is obtained at the top of the column, of HF-F32 azeotrope in which the HF weight content is lower than 2.2% (value at 6 bars absolute), but may be much lower at higher pressure. A stream (3) is obtained at the bottom of the column, consisting of HF which is in excess in relation to the azeotrope and virtually free from F32.

In the light of the above Table II it will be understood that the distillation pressure (higher than 6 bars absolute) is to be chosen as a function of the desired target purity of the F32 collected at the top; its residual HF content will be proportionally lower the higher the distillation pressure.

Since HF-F32 azeotropes of very low HF content have boiling points very close to that of F32 (−51.7° C.), distillation according to this embodiment is very easy and makes it possible, with low reflux ratios, of the order of 1 or less, to obtain at the top the azeotrope which is practically free from excess HF and at the bottom HF practically free from F32.

The distillation according to this embodiment can also be applied to the treatment of a crude mixture containing, besides HF and F32, other products or impurities such as F31, methylene chloride and the like. In this case the F31 or the $CH_2Cl_2$ move to the bottom of the column with the HF, while F32 with a low or even very low HF content is obtained at the top.

Figure 2:
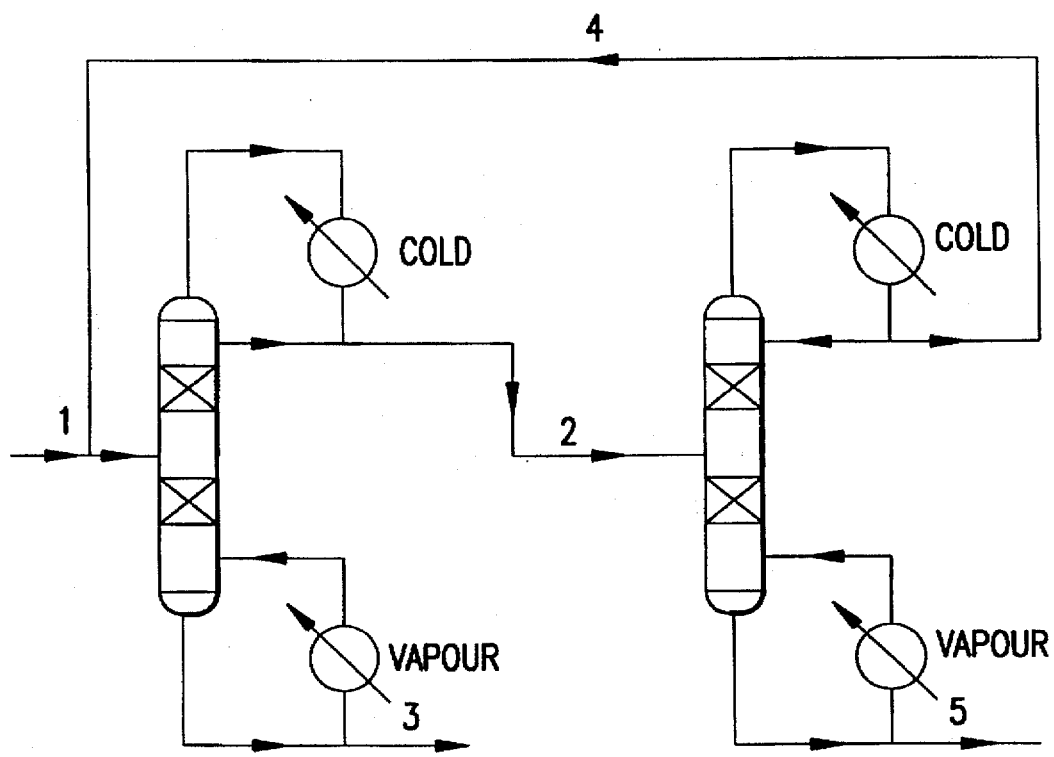

The diagram of FIG. 2 corresponds to a modification of the above method of implementation and also applies to the separation of mixtures consisting essentially of HF and of F32 to obtain virtually pure F32 and to recover HF in anhydrous form. The process according to FIG. 2, which includes two distillation stages, may be advantageously employed when, for any reasons (economical or other), the required target purity for F32 is not reached by a single distillation according to the process of FIG. 1.

In the embodiment according to FIG. 2 the mixture to be separated is first of all subjected in a first column to a distillation at an elevated pressure above 6 bars absolute, preferably above 10 bars absolute. An HF-F32 azeotrope of relatively low HF content (less than 2.2% by weight) is obtained at the top and most of the excess HF, free from F32, at the bottom. The azeotrope obtained at the top is next introduced via the conduit (2) into a second column and subjected to a distillation conducted at a lower pressure than that in the first distillation. At the top of the second distillation column an HF-F32 azeotrope is obtained with a relatively high HF content, which is recycled via the conduit (4) to the feed of the first column. A stream (5) of F32 virtually free from HF is obtained at the bottom of the second column.

Such a system is obviously proportionally more efficient the greater the pressure difference between the two distillations. The separation between the HF-F32 azeotrope and F32, performed in the second distillation column, is more difficult than that performed in the first column between the azeotrope and HF. This separation requires a higher reboiling ratio, for example of the order of 3 to 4, depending on the F32 purity required; it is made easier by a low pressure, preferably below 10 bars absolute.

As in the case of the process according to FIG. 1, the embodiment according to FIG. 2 may also be applied to the treatment of a crude mixture containing, besides HF and F32, other products or impurities (F31, $CH_2Cl_2$, and the like) which are recovered with HF at the bottom of the first distillation column.

Figure 3:
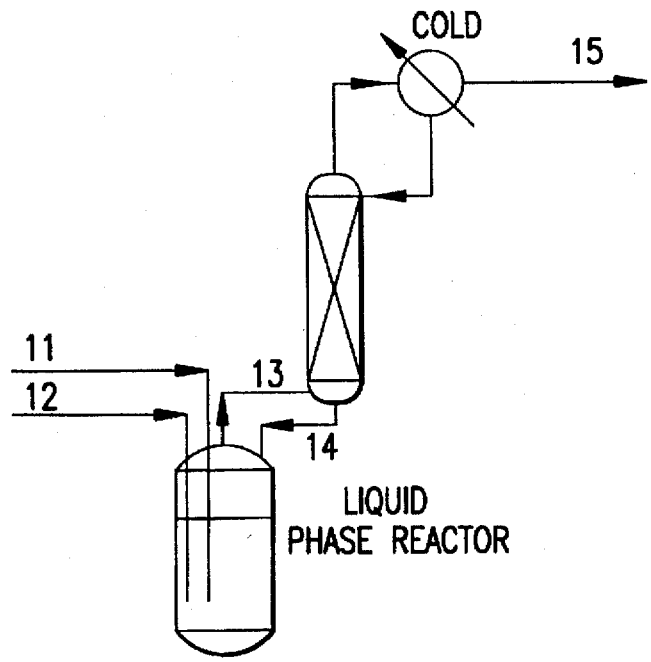

Another method of implementation, shown diagrammatically in FIG. 3, concerns more particularly the manufacture of F32 by reaction of methylene chloride with HF in liquid phase in a conventional plant including a reactor fed with fresh HF and $CH_2Cl_2$ via conduits 11 and 12 and a return device. The reaction products, which leave the reactor in gaseous form and include HCl, F32, HF and various impurities, are introduced via conduit 13 into a return column carrying a condenser above. HCl, F32 and a proportion of unconverted HF leave in gaseous form at the top of the column, while most of the heavier organic products and the remaining unconverted HF are returned to the reactor via conduit 14.

In the method of implementation according to FIG. 3 the objective of the separation between HF and F32, performed in the return device, is to minimize the outflow of HF accompanying the F32 produced and to recycle as much HF as possible directly to the reactor. To meet the objective aimed at in this separation the implementation of the process according to the invention consists in conducting the return at a pressure above 12 bars absolute, preferably between 16 and 50 bars absolute.

Despite the presence of HCl, the maximum HF content of the HF-F32-HCl mixture leaving the reaction system by conduit 15 downstream of the condenser corresponds substantially to the HF content of the HF-F32 azeotrope under the partial pressure of the HF-F32 mixture, this partial pressure being equal to the difference between the total pressure and the partial pressure of HCl. As the HF content of the azeotrope decreases strongly when the pressure increases, the maximum HF content of the HF-F32-HCl mixture leaving the reaction system decreases strongly when the total pressure at which the return is conducted increases. Thus, when operating at a pressure above 12 bars absolute, the HF content of the stream leaving the reaction system by conduit 15 is not more than 2.5% by weight, which corresponds broadly to the objective of returning most of the unconverted HF to the reactor.

Figure 4:
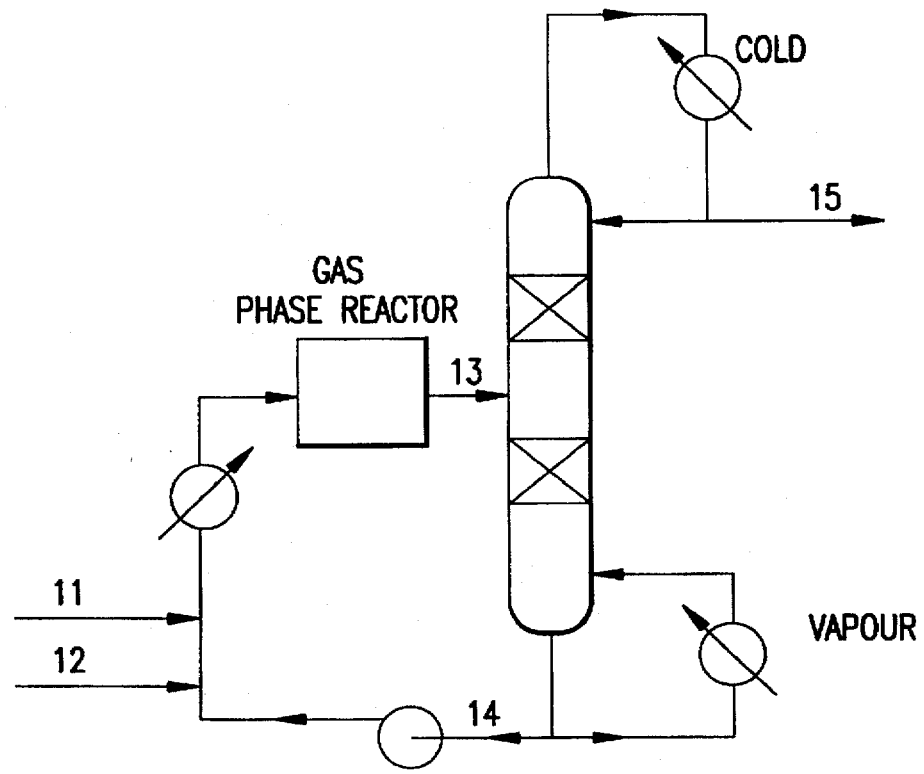

Yet another method of implementing the process according to the invention is shown diagrammatically in FIG. 4 and concerns more particularly the manufacture of F32 by reaction of methylene chloride with HF in gaseous phase. At the outlet of the reactor, fed with fresh HF and $CH_2Cl_2$ by conduits 11 and 12, a gaseous mixture of F32, HCl, HF, F31 and $CH_2Cl_2$ is obtained, which is introduced by conduit 13 into a conventional distillation column to obtain, on the one hand, at the top, a stream 15 consisting essentially of HCl and F32 and, on the other hand, at the bottom, a stream consisting essentially of HF and of underfluorinated organics (F31, $CH_2Cl_2$) which is recycled to the reactor by conduit 14.

In manufacture of this type the objective of the separation between HF and F32 which is performed in the distillation column is to minimize the HF content of the stream 15 so as to recycle most of the unconverted HF to the reaction. To meet this objective the implementation of the process according to the invention consists in conducting the distillation at a pressure above 12 bars absolute, preferably between 16 and 50 bars absolute.

As in the case of the manufacture in liquid phase, the maximum HF content in the stream 15 leaving the reaction system corresponds substantially to the HF content of the HF-F32 azeotrope under the partial pressure of the HF-F32 mixture and decreases strongly with increase in the operating pressure.

EXAMPLES

The following examples illustrate the invention without limiting it. The percentages shown are expressed on a weight basis.

Example 1

The characteristics of the HF-F32 azeotrope indicated in the above Table II have been determined by measuring the composition of the gas phase of various mixtures of HF and F32 after bringing them to equilibrium at different pressures.

The equilibration is carried out in a 102-ml stainless steel receptacle equipped with a dip pipe and a gas phase outlet. The HF-F32 mixture being studied is prepared by weighing, HF and F32 being introduced separately. HF is introduced first into the receptacle placed beforehand in a bath thermostated at −20° C. and evacuated, then the receptacle is weighed and the operation is repeated for the introduction of F32, the total volume of liquid in the receptacle representing 80 ml. After filling, the receptacle is closed and then replaced in the thermostated bath and taken to the pressure being studied. Temperature measurement and analysis of the mixture are performed 12 hours after the pressure and temperature have stabilized.

The analysis is carried out by gas chromatography on a sample of the gas phase from the mixture at equilibrium, each analysis being performed three times before the mixture is taken to a higher pressure or products are recharged.

The series of measurements performed has been collected in the following table. At each pressure a number of measurements are available which straddle the azeotrope and therefore make it possible to determine it.

| PRESSURE | TEMPERATURE | F32 Content (weight %) | |
|---|---|---|---|
| (bars absolute) | (°C.) | liquid phase | vapor phase |
| 2.7 | −26.8 | 97.10 | 97.55 |
| azeotrope | −27.1 | 98.05 | 97.60 |
|  | −27.2 | 99.47 | 98.61 |
|  | −27.3 | 99.88 | 99.73 |
|  | −27 | 97.40 | 97.40 |
| 6 | 23.3 | 20.71 | 89.63 |
| azeotrope | 2.7 | 49.24 | 96.01 |
|  | −3.2 | 79.33 | 97.21 |
|  | −6.7 | 91.27 | 97.70 |
|  | −8.2 | 97.86 | 97.86 |
|  | −8.6 | 99.02 | 98.58 |
|  | −8.8 | 99.38 | 99.10 |
|  | −8.2 | 97.80 | 97.80 |
| 10 | 45.5 | 20.71 | 90.13 |
| azeotrope | 20.2 | 49.24 | 96.82 |
|  | 12.6 | 79.33 | 97.69 |
|  | 9.8 | 91.27 | 98.28 |
|  | 9.1 | 97.86 | 98.72 |
|  | 7.2 | 99.02 | 98.98 |
|  | 7.4 | 99.38 | 99.26 |
|  | 7.2 | 99.00 | 99.00 |
| 20 | 76.6 | 20.71 | 90.75 |
| azeotrope | 53.4 | 49.24 | 97.27 |
|  | 43.8 | 79.33 | 98.47 |
|  | 35.6 | 91.27 | 99.13 |
|  | 34.5 | 97.86 | 99.65 |
|  | 33.5 | 99.02 | 99.66 |
|  | 33.2 | 99.38 | 99.68 |
|  | 33.1 | 99.70 | 99.70 |
| 31 | 52.2 | 98.05 | 99.73 |
| azeotrope | 52 | 99.47 | 99.76 |
|  | 51.9 | 99.87 | 99.89 |
|  | 51.8 | 99.90 | 99.90 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

Example 2

In accordance with the diagram in FIG. 1, a mixture of HF and of F32, containing 10% of HF is separated at 16 bars absolute in a distillation column of 10 theoretical plates.

The following table summarizes the operating conditions and the results obtained.

|  | FEED 1 | HEAD 2 | FOOT 3 |
| --- | --- | --- | --- |
| HF % | 10 | 0.45 | 100 |
| F32 % | 90 | 99.55 | 0 |
| Pressure (bars absolute) | 16 | 16 | 16 |
| Temperature (°C.) | 20 | 24 | 110 |

Example 3

A mixture of HF and of F32, containing 10% of HF is separated in the device according to FIG. 2. The first distillation is performed at 16 bars absolute and the second at 6 bars absolute. The first column has 10 theoretical plates. The second has 28 and is fed at the 22nd plate.

The operating conditions and the results obtained are summarized in the following table:

|  | FEED 1 | OUTLET 3 | STREAM 2 | STREAM 4 | OUTLET 5 |
| --- | --- | --- | --- | --- | --- |
| HF % | 10 | 100 | 0.45 | 2.2 | 0 |
| F32 % | 90 | 0 | 99.55 | 97.8 | 100 |
| Pressure (bars absolute) | 16 | 16 | 16 | 6 | 6 |
| Temperature (°C.) | 20 | 110 | 24 | −8 | −6 |

Example 4

The operation is carried out at 20 bars absolute in accordance with the diagram in FIG. 3. The return column has 6 theoretical plates.

The following table summarizes the operating conditions and the results obtained.

|  | FEED 11 | FEED 12 | FEED 15 |
| --- | --- | --- | --- |
| $CH_2Cl_2$ % | 100 | 0 | 0 |
| HF % | 0 | 100 | 0.8 |
| F32 % | 0 | 0 | 41.3 |
| HCl % | 0 | 0 | 57.9 |
| Pressure (bars absolute) | 20 | 20 | 20 |
| Temperature (°C.) | 20 | 20 | −5 |

The overall conversion ratio of HF in this reaction system is 97.5%.

Example 5

Fluorination of methylene chloride in gaseous phase at 20 bars absolute is performed in the device according to the diagram in FIG. 4. The reactor is fed continuously with fresh reactants (HF and F32) and by recycling the stream 14 originating from the foot of the distillation column which has 13 theoretical plates.

The following table summarizes the operating conditions and the results obtained.

|  | FEED 11 | FEED 12 | STREAM 13 | STREAM 14 (recycled) | OUTLET 15 |
| --- | --- | --- | --- | --- | --- |
| $CH_2Cl_2$ % | 100 | 0 | 15.3 | 28.4 | 0 |
| HF % | 0 | 100 | 29.1 | 53.2 | 0.8 |
| F31 % | 0 | 0 | 9.9 | 18.4 | 0 |
| F32 % | 0 | 0 | 19 | 0 | 41.3 |
| HCl % | 0 | 0 | 26.7 | 0 | 57.9 |
| Pressure (bars absolute) | 20 | 20 | 20 | 20 | 20 |
| Temperature (°C.) | 20 | 20 | 50 | 90 | −5 |

We claim:

1. Process for the separation of hydrogen fluoride (HF) and of difluoromethane (F32) by fractional distillation and/or condensation, in at least one stage, consisting essentially of at least one stage obtaining a stream whose HF and F32 contents correspond substantially to those of an azeotropic composition, the at least one stage being performed, as a function of the separation, at a pressure related so that the partial pressure of the HF+F32 mixture of the stream, Pa expressed in bars absolute, and the HF content of the mixture, x in per cent by weight, are linked by the relationship:

$$Pa = 17 - 22.9(x+0.821)\ln(x+0.608) + 56.6[\ln(x+0.608)]^2$$

wherein the HF content of the HF-F32 azeotrope decreases when pressure increases.

2. Process according to claim 1, for the separation of the mixture HF and F32, wherein said mixture is subjected to a first distillation conducted at a pressure above 6 bars absolute.

3. Process according to claim 2, wherein the HF-F32 azeotrope of low HF content, obtained at the top of the distillation, is subjected to a second distillation conducted at a lower pressure than that of the first distillation and the HF-F32 azeotrope of higher HF content, obtained at the top of the second distillation, is recycled to the first distillation.

4. Process according to claim 3, wherein the second distillation is performed at a pressure below 10 bars absolute.

5. Process according to claim 2, wherein the pressure is above 10 bars absolute.

6. Process according to claim 1, for the separation of a gaseous mixture originating from a reaction for producing F32 by fluorination of methylene chloride with HF in liquid phase, wherein the gaseous mixture containing F32, HF, HCl and by products and reactants of said reaction for producing F32 are subjected to a fractional distillation return or condensation operation at a pressure above 12 bars absolute.

7. Process according to claim 6, wherein the separation is performed at a pressure of between 16 and 50 bars absolute.

8. Process according to claim 1, for the separation of a gaseous mixture originating from a reaction for producing F32 by fluorination of methylene chloride with HF in gaseous phase, wherein the gaseous mixture containing F32, HF, HCl and by products and reactants of said reaction for producing F32 is subjected to a fractional distillation and/or condensation at a pressure above 12 bars absolute.

9. Process according to claim 8, wherein the separation is performed at a pressure of between 16 and 50 bars absolute.

* * * * *